United States Patent
Lim et al.

(10) Patent No.: US 12,285,512 B2
(45) Date of Patent: Apr. 29, 2025

(54) COMPOSITION COMPRISING ALLULOSE AS ACTIVE INGREDIENT FOR SKIN WHITENING

(71) Applicant: CJ CHEILJEDANG CORPORATION, Seoul (KR)

(72) Inventors: Joo Hee Lim, Yongin-si (KR); Ji Eun Park, Seoul (KR); Su Jeong Kim, Suwon-si (KR); Youn Kyung Park, Suwon-si (KR); Sung Bae Byun, Sejong (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 798 days.

(21) Appl. No.: 17/312,213

(22) PCT Filed: Dec. 13, 2019

(86) PCT No.: PCT/KR2019/017702
§ 371 (c)(1),
(2) Date: Jun. 9, 2021

(87) PCT Pub. No.: WO2020/122667
PCT Pub. Date: Jun. 18, 2020

(65) Prior Publication Data
US 2022/0047488 A1    Feb. 17, 2022

(30) Foreign Application Priority Data
Dec. 13, 2018 (KR) .................. 10-2018-0160697

(51) Int. Cl.
| | | |
|---|---|---|
| A61K 8/60 | (2006.01) | |
| A21D 2/18 | (2006.01) | |
| A23C 15/00 | (2006.01) | |
| A23G 9/34 | (2006.01) | |
| A23L 2/02 | (2006.01) | |
| A23L 2/60 | (2006.01) | |
| A23L 7/10 | (2016.01) | |
| A23L 13/40 | (2023.01) | |
| A23L 13/60 | (2016.01) | |
| A23L 23/00 | (2016.01) | |
| A23L 33/125 | (2016.01) | |
| A61K 31/7004 | (2006.01) | |
| A61P 17/00 | (2006.01) | |
| A61Q 19/02 | (2006.01) | |

(52) U.S. Cl.
CPC ............... *A61K 8/60* (2013.01); *A21D 2/181* (2013.01); *A23C 15/00* (2013.01); *A23G 9/34* (2013.01); *A23L 2/02* (2013.01); *A23L 2/60* (2013.01); *A23L 7/10* (2016.08); *A23L 13/40* (2016.08); *A23L 13/60* (2016.08); *A23L 23/00* (2016.08); *A23L 33/125* (2016.08); *A61K 31/7004* (2013.01); *A61P 17/00* (2018.01); *A61Q 19/02* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 10,246,476 B2 | 4/2019 | Kim et al. | |
| 2005/0002880 A1 | 1/2005 | Mummert | |
| 2008/0274068 A1* | 11/2008 | Tanaka | A61K 8/498 424/60 |
| 2017/0196795 A1* | 7/2017 | Hakozaki | A61K 8/361 |
| 2017/0313734 A1 | 11/2017 | Kim et al. | |
| 2018/0327796 A1 | 11/2018 | Lee et al. | |

FOREIGN PATENT DOCUMENTS

| | | | |
|---|---|---|---|
| JP | H04198115 A | 7/1992 | |
| JP | H11-335226 A | 12/1999 | |
| JP | 2004529958 A | 9/2004 | |
| JP | 2004339152 A | 12/2004 | |
| JP | 2005-263670 A | 9/2005 | |
| JP | 2005-263734 A | 9/2005 | |
| JP | 2012140376 A | 7/2012 | |
| KR | 10-2016-0046143 A | 4/2016 | |
| KR | 10-2016-0062349 A | 6/2016 | |
| WO | 2004100962 A | 11/2004 | |
| WO | WO-2004100962 A1 * | 11/2004 | A61K 31/7034 |
| WO | 2017026541 A1 | 2/2017 | |

OTHER PUBLICATIONS

Extended European Search Report dated Aug. 29, 2002 for PCT/KR2019/017702 (7 pages).
Database GNPD [Online], MINTEL, Jun. 29, 2016, anonymous: "Active Skin Gel", XP055949339, Database accession No. 4110635 (5 pages).
Database WPI, Week 200501, Thomson Scientific, London, GB, AN 2005-012793, XP002807287, WO2004/100962A1 (Nakagawa A) Nov. 25, 2004, (4 pages).
Database WPI, Week 199235, Thomas Scientific, London, GB, AN 1992-288871, XP002807288, JPH04198115A (Sansho Pharm Co LTD) Jul. 17, 1992, (1 page).
Notification of Third Party Observation issued on Oct. 13, 2002 for corresponding Japanese Patent Application 2021-533625 (3 pages).
Chinese Office Action for Chinese Application No. 201980082640.2 issued on Oct. 31, 2002 (9 pages).
Japanese Office Action for JP Application No. 2021-533625 mailed Jun. 24, 2022 (10 pages, with English translation).
International Search Report for International Application No. PCT/KR2019/017702 mailed Mar. 27, 2020 (6 pages), Including English Translation.
Han, et al., "A study of correlation between antioxidant activity and whitening effect of plant extracts", Korean Journal of Skin Beauty Education 1(1), 2003, pp. 11-22, English Abstract.

\* cited by examiner

*Primary Examiner* — Robert A Wax
*Assistant Examiner* — Quanglong N Truong
(74) *Attorney, Agent, or Firm* — Merchant & Gould P.C.

(57) ABSTRACT

The present invention relates to a cosmetic composition for skin whitening.

3 Claims, 1 Drawing Sheet

COMPOSITION COMPRISING ALLULOSE AS ACTIVE INGREDIENT FOR SKIN WHITENING

This application is a National Stage Application of PCT/KR2019/017702, filed 13 Dec. 2019, which claims benefit of Serial No. 10-2018-0160697, filed 13 Dec. 2018 in Republic of Korea and which applications are incorporated herein by reference. To the extent appropriate, a claim of priority is made to each of the above disclosed applications.

TECHNICAL FIELD

The present invention relates to a cosmetic composition for skin whitening, containing allulose as an active ingredient.

BACKGROUND ART

"Skin whitening" is to ameliorate the change in skin color caused by excessive pigmentation in the skin due to environmental changes such as ultraviolet rays, stress, abnormal hormone secretion, and pregnancy. The most important factor in this regard is melanin that is a pigment of skin.

Hyperpigmentation of the skin is caused by abnormal melanin pigment synthesis and distribution, and is caused by various factors such as free radical, hormone abnormalities in the body after inflammatory reactions of the skin, and genetic diseases. Excessive melanin deposition can cause pathological issues of skin, etc. and is recognized as a cosmetic issue such as melasma, freckles, nevus, and age spots. Therefore, interest in whitening agents that can inhibit melanin formation is increasing, and many studies are being conducted.

Regarding an association between free radical scavenging and melanogenesis inhibition, non-patent document 1 discloses a research result that a free radical scavenging substance does not always inhibit melanogenesis, and no association between free radical scavenging activity and whitening can be found. Moreover, as an example related to the lack of association between free radical scavenging activity and whitening, hot water extract of *Epimedium koreanum* has excellent antioxidant activity, but it is known that the hot water extract increases melanin production.

As described above, even if a substance has an antioxidant effect, it is not known whether the substance exhibits a whitening effect by inhibiting melanin synthesis. Therefore, since the antioxidant effect does not always lead to a whitening effect, even if a substance is proved to have an antioxidant effect, it is necessary to further verify whether or not the substance has a whitening effect in order to use this substance for whitening purposes.

Meanwhile, allulose is also referred to as psicose, and is ketohexose (sugar with six carbon atoms). Allulose is a natural sugar that exists in a very small amount in the isomerization process of fruits such as figs and raisins, and molasses or glucose, and is a monosaccharide with a sweetness of 70% compared to sugar. Allulose is known to have an antioxidant effect like a typical reducing sugar. For example, Patent Document 1 discloses a prophylactic or therapeutic agent of a neurodegenerative disease using the neuroprotective action of allulose, and indicates that allulose exhibits an antioxidant activity because the neuroprotective action of allulose results from suppressing the injury caused by oxidation of neurons, but there are no known whitening-related effects of allulose, for example, a melanogenesis inhibitory effect or a tyrosinase activity inhibitory effect.

The present inventors studied raw materials with a whitening function, confirmed that allulose actually exhibits an effect directly on skin whitening from noting that even a material with an antioxidant effect does not necessarily exhibit a whitening effect, and confirmed that allulose inhibits melanogenesis and tyrosinase activity, and thus completed the present invention.

PRIOR ART DOCUMENTS (Patent Document 1) Japanese Laid-open Patent No. 2005-263734

(Non-Patent Document 1) Young-sook Han et al., A study of correlation between antioxidant activity and whitening effect of plant extracts, Korean Journal of Skin Beauty Education 1(1), 11-22 (2003)

DISCLOSURE OF THE INVENTION

Technical Problem

The object of the present invention is to provide a novel active ingredient having an excellent whitening effect.

Technical Solution

According to an aspect in order to attain the purpose of the present application, there is provided a composition for skin whitening containing allulose as an active ingredient.

The allulose of the present application fundamentally inhibits melanogenesis, and thus may provide an excellent whitening effect, and may ameliorate skin pigmentation and skin tone darkening. The skin whitening refers to any action that inhibits or prevents the skin pigmentation of melanin by inhibiting melanogenesis, and the skin pigmentation of melanin refers to any action or condition of darkening the color of the skin due to increased melanogenesis.

The allulose of the present application may be produced by a chemical synthesis or a biological method, and particularly, may be produced by a biological method. Thus, the allulose may be produced by making a composition for producing allulose, the composition containing at least one selected from the group consisting of an epimerization enzyme, a bacterial cell of a strain producing the enzyme, a culture of the strain, a lysate of the strain, and an extract of the lysate or culture, react with a fructose-containing raw material. In addition, the allulose may be provided in a liquid or crystalline form. The liquid allulose may contain 70 to 99 wt % of an allulose based on dry solids (ds or DS). Crystal allulose may also contain 90 wt % to 100 wt % of an allulose based on dry solids.

The allulose of the present application may be contained in a content of 0.2-60 wt % in the cosmetic composition, for example, 0.3-50 wt %, 0.4-45 wt %, 0.5-40 wt %, 0.6-35 wt %, 0.7-30 wt %, 0.8-25 wt %, 0.9-20 wt %, 1-20 wt %, 1-10 wt %, 1-8 wt %, 1-5 wt %, 1-3 wt %, 1-2 wt %, and 1-1.5 wt %. When the content of allulose in the cosmetic composition is less than 0.2 wt %, the whitening effect by allulose may not be sufficiently expressed, and when the content is more than 60 wt %, the effect by allulose may be relatively low for the input concentration.

The skin whitening may be performed by inhibiting pigmentation caused by melanogenesis, or inhibiting pigmentation by inhibiting tyrosinase activity.

In an embodiment of the present application, it was confirmed that melanocytes were treated with 1 wt % of allulose to inhibit melanogenesis. From this, it can be seen that the allulose exhibits a whitening effect through the melanogenesis inhibitory effect.

A skin whitening composition containing allulose of the present application as an active ingredient may be a cosmetic composition, a food composition, or a pharmaceutical composition.

The cosmetic composition of the present application may be prepared in a liquid or solid form using bases, adjuvants, and additives commonly used in the cosmetic field. Cosmetics in liquid or solid form may include, for example, but not limited to, a form such as face lotion, cream, lotion, and bath agent. Bases, adjuvants, and additives commonly used in the cosmetic field are not particularly limited, and include, for example, water, alcohol, propylene glycol, stearic acid, glycerol, cetyl alcohol, liquid paraffin, etc.

The cosmetic composition of the present application may include not only allulose, but also components commonly used in a cosmetic composition, and may include, for example, typical adjuvants such as antioxidants, stabilizers, solubilizers, vitamins, pigments, and fragrances, and carriers.

The cosmetic composition of the present application may be prepared in any formulation typically prepared in the art, and for example, may be formulated in solution, suspension, emulsion, paste, gel, cream, lotion, powder, soap, surfactant-containing cleanser, oil, powder foundation, emulsion foundation, wax foundation and spray, but is not limited thereto. More specifically, it may be prepared in the formulation of skin softener, nutrition lotion, nutrition cream, massage cream, essence, eye cream, cleansing cream, cleansing foam, cleansing water, pack, spray, or powder.

When the formulation of the cosmetic composition of the present application is paste, cream, or gel, animal oil, vegetable oil, wax, paraffin, starch, tragacanth, cellulose derivatives, polyethylene glycol, silicone, bentonite, silica, talc or zinc oxide may be used as a carrier component.

When the formulation of the cosmetic composition of the present application is powder or spray, lactose, talc, silica, aluminum hydroxide, calcium silicate, or polyamide powder may be used as a carrier component, and particularly, when it is spray, a propellant such as chlorofluorohydrocarbon, propane/butane or dimethyl ether may be contained.

When the formulation of the cosmetic composition of the present application is solution or emulsion, a solvent, a solubilizing agent or an emulsifying agent is used as a carrier component, for example, water, ethanol, isopropanol, ethyl carbonate, ethyl acetate, benzyl alcohol, benzyl benzoate, propylene glycol, 1,3-butylene glycol oil, glycerol aliphatic ester, polyethylene glycol, or sorbitan fatty acid ester.

When the formulation of the cosmetic composition of the present application is suspension, a liquid diluent such as water, ethanol or propylene glycol, a suspending agent, such as ethoxylated isostearyl alcohol, polyoxyethylene sorbitol ester, polyoxyethylene sorbitan ester, microcrystalline cellulose, aluminum metahydroxide, bentonite, agar, tragacanth, or the like may be used as a carrier component.

When the formulation of the cosmetic composition of the present application is a surfactant-containing cleanser, aliphatic alcohol sulfate, aliphatic alcohol ether sulfate, sulfosuccinic monoester, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, ethoxylated glycerol fatty acid ester, or the like may be used as a carrier component.

The cosmetic composition of the present application may be used alone or in conjunction with other composition, or may be applied in combination with other cosmetic compositions other than the present invention. In addition, the cosmetic composition having excellent skin moisturizing effect and skin barrier improvement effect according to the present invention may be used according to a typical method, and the frequency of use thereof may vary depending on the skin condition or taste of the user.

When the cosmetic composition of the present application is formulated as a soap, a surfactant-containing cleansing, or a surfactant-free cleansing formulation, it may be applied to the skin and then wiped off, removed, or washed out with water. As specific examples, the soap includes, but is not limited to, liquid soap, powder soap, solid soap and oil soap, the surfactant-containing cleansing formulation includes, but is not limited to, cleansing foam, cleansing water, a cleansing towel and a cleansing pack, and the surfactant-free cleansing formulation includes, but is not limited to, cleansing cream, cleansing lotion, cleansing water and cleansing gel.

The food composition of the present application may be provided in the form of powder, granule, tablet, capsule, syrup or beverage, and the food composition is used with other foods or food additives in addition to the allulose of the present application, which is an active ingredient, and may be used appropriately according to a typical method. The mixed amount of the active ingredient may be appropriately determined according to the purpose of use, for example, prevention, health or therapeutic treatment.

The effective amount of allulose contained in the food composition of the present application may be used based on the effective amount of the cosmetic composition, but may be equal to or less than the above range in the case of long-term ingestion for the purpose of health and hygiene or health control, and since there is no problem in terms of safety, it is clear that the active ingredient can be used in an amount equal to or more than the above range.

There is no particular limitation on types of the food of the present application, and examples include meat, sausage, bread, chocolate, candy, snacks, confectionery, pizza, ramen, other noodles, gums, dairy products including ice cream, various soups, beverages, tea, health drinks, alcoholic beverages, and vitamin complexes.

The pharmaceutical composition of the present application may further include suitable carriers, excipients, or diluents commonly used in the preparation of pharmaceutical compositions.

Carriers, excipients or diluents which can be used in the pharmaceutical composition of the present application include lactose, dextrose, sucrose, sorbitol, mannitol, xylitol, erythritol, maltitol, starch, gum acacia, alginates, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil, or the like.

The pharmaceutical composition of the present application may be formulated and used in the form of an oral dosage form such as powder, granule, tablet, capsule, suspension, emulsion, syrup, aerosol, an external preparation, a suppository, and a sterile injection solution, according to a typical method.

When formulated, the pharmaceutical composition is prepared with generally used diluents or excipients such as fillers, extenders, binders, wetting agents, disintegrating agents, and surfactants. Solid formulations for oral administration include tablets, pills, powders, granules, capsules, and the like, and such solid preparations may be prepared by mixing the compound with at least one excipient, for example, starch, calcium carbonate, sucrose or lactose, gelatin, etc.

In addition to simple excipients, lubricants such as magnesium stearate and talc are also used. Liquid formulations for oral administration include suspensions, solutions, emulsions, syrups, etc., and in addition to water and liquid paraffin, which are commonly used simple diluents, various excipients such as wetting agents, sweetening agents, fragrances, and preservatives may be included.

Formulations for parenteral administration include sterilized aqueous solutions, non-aqueous solvents, suspensions, emulsions, lyophilized formulations, and suppositories. As the non-aqueous solvents and suspensions, propylene glycol, polyethylene glycol, vegetable oil such as olive oil, and an injectable ester such as ethyl oleate, etc. may be used. As a base for the suppositories, Witepsol, macrogol, Tween 61, cacao butter, laurinum, glycerogelatin, etc. may be used.

Solid formulations for oral administration include tablets, pills, powders, granules, capsules, and the like, and such solid preparations may be prepared by mixing at least one excipient, for example, starch, calcium carbonate, sucrose or lactose, gelatin, etc. to the pharmaceutical composition of the present application. In addition to simple excipients, lubricants such as magnesium stearate and talc may also be used.

Liquid formulations for oral administration include suspensions, solutions, emulsions, syrups, etc., and in addition to water and liquid paraffin, which are commonly used simple diluents, various excipients such as wetting agents, sweetening agents, fragrances, and preservatives may be included.

Formulations for dermal administration may be dusting powders, emulsions, suspensions, oils, sprays, ointments, cream pastes, gels, foams, or solutions. The pharmaceutical formulation of the present application may be an anhydrous ointment, may contain a paraffin, especially low viscosity paraffin which is suitable for topical use and in liquid state at body temperature, or the natural or partially synthetic fats, e.g., coconut fatty acid triglyceride, hardened oils, e.g. hydrogenated peanut oil or castor oil, fatty acid partial esters of glycerol, e.g. glycerol monostearate and glycerol distearate, silicones, e.g., polymethylsiloxane such as hexamethyl disiloxane or octamethyltrisiloxane, and e.g. the fatty alcohols in connection with the aqueous creams and increasing uptake of water, and sterols, wool waxes, other emulsifiers and/or other additives.

The applied amount of allulose contained in the pharmaceutical composition of the present application varies depending on the condition and body weight of a patient, the severity of the disease, the form of drug, and the route and duration of administration, but may be appropriately selected depending on the case. For example, the allulose may be administered at a dose of 0.0001 to 1,000 mg/kg per day, specifically 0.1 to 1,000 mg/kg, and the application may be applied once or several times for a total daily dose. The dosage of allulose of the present application may be increased or decreased depending on the route of administration, the severity of the disease, sex, body weight, age, and the like. Therefore, the dosage does not limit the scope of the present application in any way.

The pharmaceutical composition of the present application may be administered in various routes to mammals such as rats, mice, livestock, and humans. All modes of administration may be expected, for example, by oral, rectal or intravenous, intramuscular, subcutaneous, intrabronchial inhalation, intrauterine dura or intracerebroventricular injection.

As one aspect for achieving the object of the present application, the present application provides a composition for preventing, inhibiting or treating pigmentation diseases.

The composition for preventing, inhibiting or treating pigmentation diseases of the present application includes allulose as an active ingredient. The allulose acts on hyperpigmented skin to reduce melanin deposited on the skin through the inhibition of melanogenesis, thereby effectively eliminating diseases and lesions associated with pigmentation. The purity of allulose applicable to the present invention is as described above.

As used herein, the term "prevention" refers to any action that delays the onset of a pigmentation disease by the composition of the present application.

As used herein, the term "inhibition" refers to any action that reduces the onset of a pigmentation disease by the composition of the present application.

As used herein, the term "treatment" refers to any action that ameliorates or beneficially changes the symptoms of a pigmentation disease by the composition of the present application.

As used herein, the term "administration" refers to introducing a predetermined substance to a subject by any suitable method, and the composition of the present application may be administered through any general route capable of reaching a target in vivo. The route of administration of the composition of the present application is not particularly limited, but may be administered orally or parenterally. Specifically, it may be administered parenterally, and more specifically, it may be applied to the skin (i.e., transdermal administration). Specifically, the administration of the present application may be carried out one to four times, two to three times, or two times per day. In addition, the administration of the present application may be carried out for a period of 4 weeks or more, 8 weeks or more, 4 weeks to 12 weeks, or 8 weeks to 12 weeks.

The pigmentation disease may include, without limitation, all diseases and lesions that may be caused by melanin produced abnormally in the skin. Specifically, freckles, senile plaque, liver spots, melasma, brown or black spots, sun pigment spots, cyanic melasma, hyperpigmentation after drug use, malignant melanoma, Ota nevus, giant nevus, gravidic chloasma, or hyperpigmentation after inflammation due to wounds or dermatitis including abrasions and burns.

The composition for preventing, inhibiting, or treating the pigmentation diseases may be a cosmetic composition, a food composition, or a pharmaceutical composition. The dosages of the cosmetic composition, food composition, and pharmaceutical composition are as described above.

In addition, the composition for preventing, inhibiting, or treating the pigmentation diseases contains 0.2-60 wt % of allulose, for example, 0.3-50 wt %, 0.4-45 wt %, 0.5-40 wt %, 0.6-35 wt %, 0.7-30 wt %, 0.8-25 wt %, 0.9-20 wt %, 1-20 wt %, 1-10 wt %, 1-8 wt %, 1-5 wt %, 1-3 wt %, 1-2 wt %, 1-1.5 wt %, based on the total weight of the composition. When the content of the allulose in the cosmetic composition is less than 0.2 wt %, the effect of preventing, inhibiting, or treating pigmentation diseases by means of allulose may not be sufficiently exhibited, and when the content is more than wt %, the effect of allulose may be relatively low compared to the input concentration.

The composition for preventing, inhibiting, or treating pigmentation diseases of the present application may contain one or more active ingredients exhibiting improvement, alleviation, treatment, or prevention of skin pigmentation in addition to allulose.

The composition for preventing, inhibiting, or treating pigmentation diseases of the present application may be used alone or in combination with methods of using surgery, hormone treatment, drug treatment, and a biological response modifier for improvement, alleviation, treatment or prevention of skin pigmentation.

As one aspect for achieving the object of the present application, the present application provides a composition for inhibiting tyrosinase activity, containing allulose.

The allulose of the present activity inhibits tyrosinase activity, and thus may provide an excellent whitening effect, and may ameliorate skin pigmentation and skin tone darkening. The skin whitening refers to any action that inhibits or prevents the skin pigmentation of melanin by inhibiting melanogenesis, and the skin pigmentation of melanin refers to any action or condition of darkening the color of the skin due to increased melanogenesis.

The composition for inhibiting tyrosinase activity of the present application, containing allulose as an active ingredient may be a cosmetic composition, a food composition, or a pharmaceutical composition.

The description of the cosmetic composition, the food composition, or the pharmaceutical composition will be omitted because the description is the same as described above.

As another aspect for achieving the object of the present application, the present application provides a skin whitening method comprising administering to a subject in need thereof an effective amount of allulose.

As used herein, the term "subject" may be a subject including a human or a subject other than a human.

As another aspect for achieving the object of the present application, the present application provides a skin whitening method comprising applying, to a skin or pigmented skin, the cosmetic composition for skin whitening.

In addition, the present invention provides a skin whitening method comprising feeding, to a subject or a subject having pigmented skin, the food composition for skin whitening.

In addition, the present invention provides a skin whitening method comprising administering, to a subject or a subject having pigmented skin, the pharmaceutical composition for skin whitening.

The cosmetic composition for skin whitening, the food composition for skin whitening, the pharmaceutical composition for skin whitening, and administration thereof are as described above.

The allulose of the present application can be applied, fed, or administered to a subject in need thereof in an effective amount.

As still another aspect for achieving the object of the present application, the present application provides a method for preventing or treating a pigmentation disease, the method comprising administering to a subject in need thereof an effective amount of allulose.

As still yet another aspect for achieving the object of the present application, the present application provides a method for preventing a pigmentation disease, the method comprising administering to a subject in need thereof the composition for preventing or treating a pigmentation disease.

The present application also provides a method for inhibiting a pigmentation disease, the method comprising administering to a subject in need thereof the composition for preventing or treating a pigmentation disease.

In addition, the present application provides a method for treating a pigmentation disease, the method comprising administering to a subject having a pigmentation disease the composition for preventing or treating a pigmentation disease.

The pharmaceutical composition for preventing or treating a pigmentation disease and administration thereof are as described above.

The allulose of the present application may be administered to a subject in need thereof in an effective amount.

As still yet another aspect for achieving the object of the present application, the present application provides a skin whitening method comprising applying, to a skin or pigmented skin, the cosmetic composition for inhibiting tyrosinase activity.

The present application also provides a skin whitening method comprising feeding, to a subject or a subject having pigmented skin, the food composition for inhibiting tyrosinase activity.

In addition, the present application provides a skin whitening method comprising administering, to a subject or a subject having pigmented skin, the pharmaceutical composition for inhibiting tyrosinase activity.

The composition for inhibiting tyrosinase activity, the food composition for inhibiting tyrosinase activity, the pharmaceutical composition for inhibiting tyrosinase activity, and administration thereof are as described above.

The allulose of the present application can be applied, fed, or administered to a subject in need thereof in an effective amount.

As still yet another aspect for achieving the object of the present application, the present application provides allulose for use in skin whitening.

As still yet another aspect for achieving the object of the present application, the present application provides allulose for use in the prevention or treatment of a pigmentation disease.

As still yet another aspect for achieving the object of the present application, the present application provides the use of allulose for use in the manufacture of products, foods, cosmetics, or medicines for skin whitening.

As still yet another aspect for achieving the object of the present application, the present application provides the use of allulose for use in the manufacture of products, foods, cosmetics, or medicines for the prevention or treatment of a pigmentation disease.

Advantageous Effects

Allulose, an active ingredient of the present application, exhibits not only an antioxidant activity, but also an activity that inhibits melanogenesis, and this has been clearly confirmed through a specific experiment, and thus can be used as an active ingredient of a composition for skin whitening.

However, the effect of the present application is not limited to the above-mentioned effect, and other effects not mentioned above will be clearly understood by those skilled in the art from the following description.

MODE FOR CARRYING OUT THE INVENTION

Hereinafter, the present invention will be described in detail with reference to Preparation Examples and Experimental Examples.

However, Preparation Examples and Experimental Examples below may be exemplified merely as illustrative purpose, and thus the contents of the present application are not limited thereto.

Experimental Example 1. Confirmation of Inhibitory Effect of Allulose on Melanogenesis Murine melanocytes were seeded on each 6-well plate at $1 \times 10^4$ cells/well. In a sample treatment group 24 hours after the seeding, cells were treated with allulose (CJ CheilJedang, 98% or higher purity) at a concentration of 0.01 wt %, 0.1 wt %, and 1 wt %. In a positive control group, cells were treated with arbutin at 0.02 wt %. A comparative group was treated with 1 wt % of glucose (Sigma Aldrich) or 1 wt % of fructose (Sigma Aldrich). An untreated group (control) was not treated with a sample, or a-MSH inducing melanin production. The sample treatment group, the positive control group, the comparative group, and the negative control group were treated with 50 μM of a-MSH. After 72 hours of treatment, cells were recovered and lysed with NaOH to detect intracellular melanin. The absorbances ($OD_{405}$) of the untreated group, the negative control group (treated with only a-MSH), the sample treatment group (treated with a-MSH and each sample by concentration), and the positive control group (treated with a-MSH and arbutin) were measured.

Figure 1:
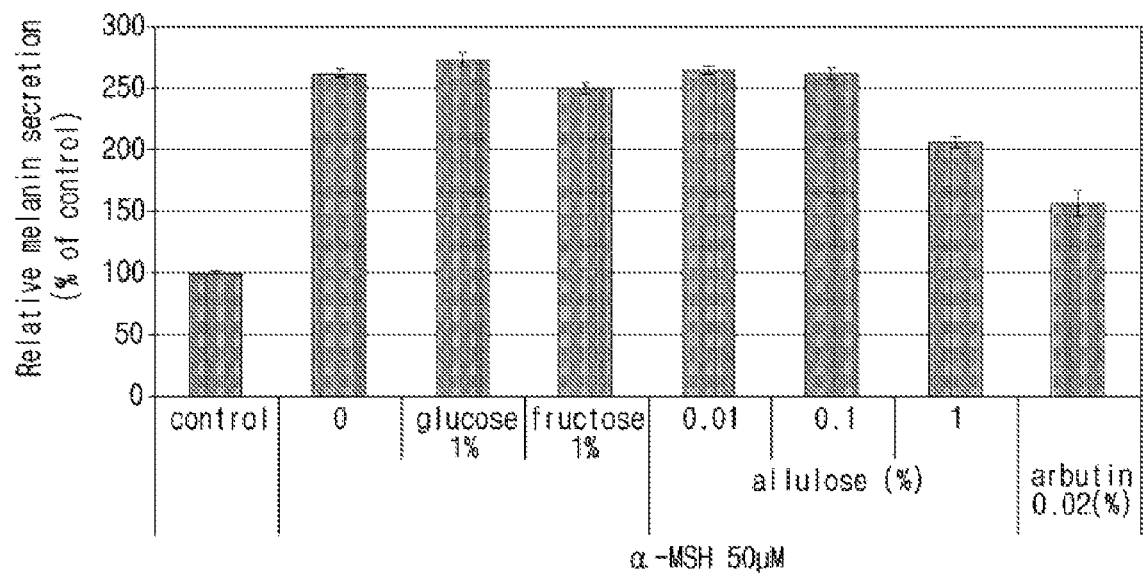
FIG. 1 is a graph showing the result of quantifying the amount of melanin released from murine melanocytes.

As a result, as shown in FIG. 1, it was confirmed that melanogenesis was suppressed in the allulose-treated group, resulting in a whitening effect. In particular, it was confirmed that melanogenesis was significantly inhibited when allulose was 1 wt %.

On the other hand, in the case of glucose and fructose which are the same saccharides as allulose and are known to have antioxidant activity, it was confirmed that melanogenesis was not inhibited at all even when the comparative group was treated at a concentration of 1 wt % of each of glucose and fructose. In addition, from the above results, it can be seen that not all substances exhibiting antioxidant activity exhibit melanogenesis inhibitory effect or whitening effect, and from this, the whitening effect through the melanogenesis inhibitory effect of allulose is not naturally derived from antioxidant activity.

Experimental Example 2. Confirmation of Inhibitory Effect of Allulose on Tyrosinase The following experiment was performed to confirm the tyrosinase inhibitory effect, which is one of the mechanisms of the whitening effect.

Experimental Example 2-1. Measurement of Polyphenol Oxidase (Tyrosinase from Mushroom) Activity An enzyme solution was prepared by dissolving 0.2 mg/ml of tyrosinase from mushroom (25 KU, 2687 units/mg solid) in 50 mM sodium phosphate buffer (pH 6.5). Allulose (Example), sucrose (Comparative Example 1), and fructose (Comparative Example 2) were each prepared at 50 mM. As a substrate, 30 mM catechol, an enzyme solution, and 100 mM sodium phosphate buffer (pH 6.5) were mixed so that the mixing ratio of catechol:enzyme solution:sodium phosphate buffer was 5:1:4. The allulose, sucrose, and fructose were each added to the mixture at 50 mM. As a co-sample solution, DW was added instead of the enzyme solution. After mixing, absorbance was measured at 420 nm.

Figure 2:
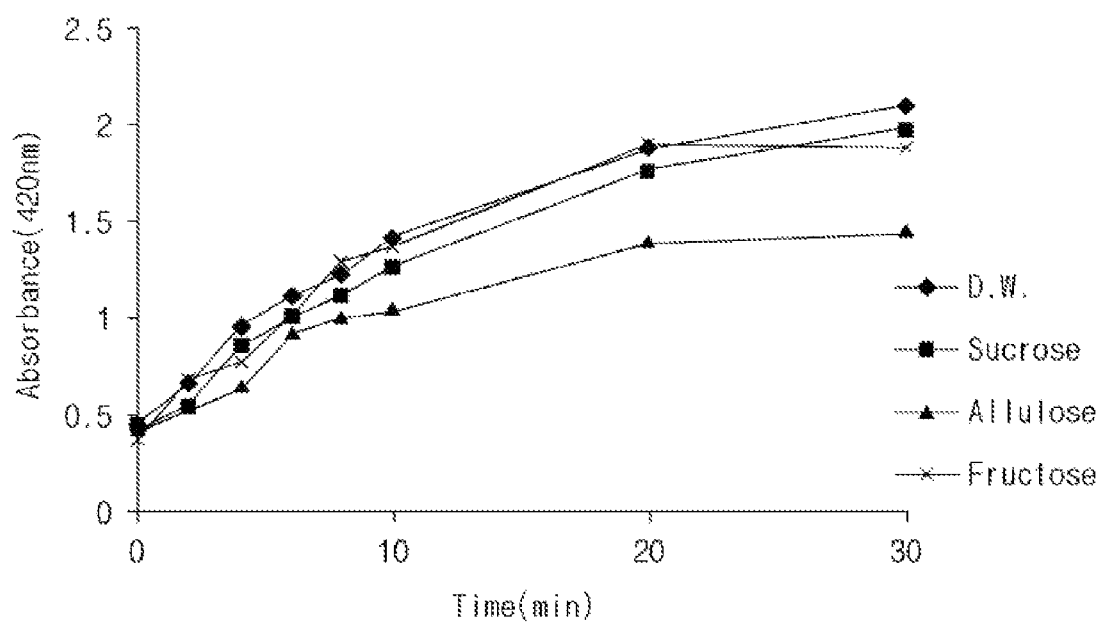
FIG. 2 is a graph showing the inhibitory effect of allulose on tyrosinase activity.

As a result, tyrosinase activity was inhibited in Example as shown in FIG. 2. On the other hand, it was confirmed that the tyrosinase activity was not inhibited at all in the case of Comparative Examples 1 and 2 known as saccharides having antioxidant activity.

Experimental Example 2-2. Quantitative Analysis of Substrate (Catechol) of Enzyme Reactant A catechol standard preparation was diluted according to concentration, and then was subjected to LC analysis to obtain a standard curve of the catechol. 200 μl of each enzyme reaction solution obtained in Experimental Example 2-1 above was added into a PCR tube, and was reacted at 37° C. for 0 minutes (an enzyme reaction product in which the enzyme was inactivated by heating each enzyme reaction solution for 10 minutes), 10 minutes, 20 minutes, 30 minutes, and 60 minutes to prepare an enzyme reactant for each reaction time. The reaction was stopped using a heat block. The reaction was stopped according to the planned time and heated in a heat block at 105° C. for 10 minutes, and then put in ice and cooled for 10 minutes. The PCR tube was centrifuged twice using a centrifuge. LC analysis was carried out by a typical analytical method. The enzyme reactant was filtered with a 1-ml syringe. The filtered enzyme reactant was injected into an insert, and was subjected to LC analysis. The amount of catechol in the enzyme reactant was measured according to the standard curve, which is obtained in advance, for quantifying catechol. LC analysis conditions are shown in Table 1 below, and the analysis results are shown in Table 2.

TABLE 1

| Column | Platinum EPS C18 100 Å 3micro u |
| --- | --- |
| Solvent | 70% Acetonitrile |
| Flow rate | 1.0 mL/min |
| Injection volume | 25 μl |
| Pump temp. | 35° C. |
| Analysis time | 15 min |
| Detector | DAD 254 nm, 280 nm |

TABLE 2

| Reaction time (min) | D.W. | Comparative Example 1 | Example | Comparative Example 2 |
| --- | --- | --- | --- | --- |
| 0 | 3292.0 | 3296.7 | 3288.7 | 3236.0 |
| 30 | 3103.0 | 3112.0 | 3126.7 | 3069.0 |
| 60 | 3022.0 | 3031.0 | 3087.0 | 2971.0 |
| Reduction rate of catechol compared to initial stage of reaction | 8.2% | 8.1% | 6.1% | 8.2% |

(Unit: ppm) As a result, the tyrosinase activity was inhibited in Example as shown in Table 2. On the other hand, it was confirmed that the tyrosinase activity was not inhibited at all in the case of Comparative Examples 1 and 2 known as saccharides having antioxidant activity.

Preparation Example 1. Preparation of Cosmetic Formulation 1-1. Preparation of Essence An essence was prepared using allulose according to the content (parts by weight) shown in Table 3 below.

TABLE 3

| Composition | Content (parts by weight) |
| --- | --- |
| Triethanolamine | 0.25 |
| Carboxyvinyl polymer | 0.22 |
| Glycerin | 4 |
| Butylene glycol | 2 |
| Allulose | 1.5 |
| Cera | 0.5 |
| Cetostearyl alcohol | 1 |
| Glyceryl monostearate | 1 |
| Squalene | 4 |
| Purified water | Suitable amount |

1-2. Preparation of Skin Softener

A skin softener containing allulose as an active ingredient was prepared as described in Table 4 below.

TABLE 4

| Raw material | Content (parts by weight) |
| --- | --- |
| 1,3-butylene glycol | 1.00 |
| Disodium EDTA | 0.05 |
| Allantoin | 0.10 |
| Dipotassium glycyrrhizate | 0.05 |
| Citric acid | 0.01 |
| Sodium citrate | 0.02 |
| Glycereth-26 | 1.00 |
| Arbutin | 2.00 |
| PEG-40 Hydrogenated castor oil | 1.00 |
| Ethanol | 30.00 |
| Allulose | 1.5 |
| Colorant | Trace |
| Fragrance | Trace |
| Purified water | Remainder |

1-3. Preparation of Nutrition Cream

A nutrition cream containing allulose as an active ingredient was prepared as the composition of Table 5 below.

TABLE 5

| Raw material | Content (parts by weight) |
| --- | --- |
| 1,3-butylene glycol | 7.0 |
| Glycerin | 1.0 |
| D-panthenol | 0.1 |
| Magnesium aluminum silicate | 0.3 |
| PEG-40 stearate | 1.2 |
| Stearic acid | 2.0 |
| Polysorbate 60 | 1.5 |
| Lipophilic glyceryl stearate | 2.0 |
| Sorbitan sesquioleate | 1.5 |
| Cetearyl alcohol | 3.0 |
| Mineral oil | 4.0 |
| Squalene | 3.8 |
| Allulose | 1.5 |
| Vegetable oil | 1.8 |
| Dimethicone | 0.4 |
| Dipotassium glycyrrhizate | Trace |
| Allantoin | Trace |
| Sodium hyaluronate | Trace |
| Tocopheryl acetate | Suitable amount |

TABLE 5-continued

| Raw material | Content (parts by weight) |
| --- | --- |
| Triethanolamine | Suitable amount |
| Fragrance | Suitable amount |
| Purified water | Remainder |

1-4. Preparation of Lotion

A lotion containing allulose as an active ingredient was prepared as the composition of Table 6 below.

TABLE 6

| Raw material | Content (parts by weight) |
| --- | --- |
| Cetostearyl alcohol | 1.6 |
| Stearic acid | 1.4 |
| Lipophilic glyceryl monostearate | 1.8 |
| PEG-100 stearate | 2.6 |
| Sorbitan sesquioleate | 0.6 |
| Squalene | 4.8 |
| Macadamia nut oil | 2 |
| Jojoba oil | 2 |
| Tocopherol acetate | 0.4 |
| Methylpolysiloxane | 0.2 |
| Tocopherol acetate | 0.4 |
| 1,3-butylene glycol | 4 |
| Xanthan gum | 0.1 |
| Glycerin | 4 |
| D-panthenol | 0.15 |
| Allulose | 1.0 |
| Allantoin | 0.1 |
| Carbomer (2% aq. Sol) | 4 |
| Triethanolamine | 0.15 |
| Ethanol | 3 |
| Purified water | Suitable amount |

Preparation Example 2. Preparation of Food 2-1. Preparation of Wheat Flour Foods 0.5-5.0 parts by weight of allulose of the present invention was added to wheat flour, and this mixture was used to prepare bread, cake, cookies, crackers, and noodles.

2-2. Preparation of Soups and Gravies 0.2-5.0 parts by weight of allulose of the present invention was added to soups and gravies to prepare soups and gravies for meat products and noodles for enhancing health.

2-3. Preparation of Ground Beef 10 parts by weight of allulose of the present invention was added to ground beef to prepare ground beef for enhancing health.

2-4. Preparation of Dairy Products 5 to 10 parts by weight of allulose of the present invention was added to milk, and the milk was used to prepare various dairy products such as butter and ice cream.

2-5. Preparation of Cereal Flour Foods

Brown rice, barley, glutinous rice, and adlay were gelatinized and dried by a known method, and the resulting product was roasted and then prepared into a powder having a particle size of 60 mesh with a pulverizer.

Black beans, black sesame seeds, and perilla seeds were also steamed and dried by a known method, and the resulting product was roasted and then prepared into a powder having a particle size of 60 mesh with a pulverizer.

The dried product obtained by concentrating the allulose of the present invention under reduced pressure in a vacuum concentrator, and drying the concentrated allulose with a spray hot air dryer was pulverized into a particle size of 60 mesh with a pulverizer to obtain a dry powder.

The above-prepared cereals, seeds and allulose of the present invention were blended in the following ratio to prepare cereal flour foods:

Cereals (30 parts by weight of brown rice, 15 parts by weight of adlay, and 20 parts by weight of barley), seeds (7 parts by weight of perilla seeds, 8 parts by weight of black beans, and 7 parts by weight of black sesame), allulose of the present invention (3 parts by weight), *Ganoderma lucidum* (0.5 parts by weight), and *Rehmannia glutinosa* (0.5 parts by weight)

2-6. Preparation of Health Drinks

Minor ingredients such as high-fructose corn syrup (0.5%), oligosaccharide (2%), sugar (2%), salt (0.5%), and water (75%), and 5 g of allulose of the present invention were uniformly blended and flash pasteurized, and then the mixture was packaged in a small container such as a glass bottle or a plastic bottle to prepare health drinks.

2-7. Preparation of Vegetable Juices 5 g of allulose of the present invention was added to 1,000 mL of a tomato or carrot juice to prepare vegetable juices.

2-8. Preparation of Fruit Juices 5 g of allulose of the present invention was added to 1,000 mL of an apple or grape juice to prepare fruit juices.

Preparation Example 3. Preparation of Pharmaceutical Composition 3-1. Preparation of Powder
  2 g of allulose of the present invention
  1 g of lactose The ingredients above were mixed and filled into an airtight packet to prepare a powder.

3-2. Preparation of Tablets
  100 mg of allulose of the present invention
  100 mg of corn starch
  100 mg of lactose
  2 mg of magnesium stearate The ingredients above were mixed, and then tableted according to a typical tablet preparation method to prepare a tablet.

3-3. Preparation of Capsules
  100 mg of allulose of the present invention
  100 mg of corn starch
  100 mg of lactose
  2 mg of magnesium stearate The ingredients above were mixed, and then filled into a gelatin capsule according to a typical capsule preparation method to prepare a capsule.

3-4. Preparation of Pills
  1 g of allulose of the present invention
  1.5 g of lactose
  1 g of glycerin
  0.5 g of xylitol After the ingredients above were mixed, pills were prepared to be 4 g per one pill according to a typical method.

3-5. Preparation of Granules
  150 mg of allulose of the present invention
  50 mg of soybean extract
  200 mg of glucose
  600 mg of starch After the ingredients above were mixed, 100 mg of 30% ethanol was added thereto and dried at 60° C. to form granules, and then the granules were filled into packets.

The invention claimed is:

1. A method of whitening skin, the method comprising administering a composition comprising an effective amount of allulose to a subject in need thereof, wherein the allulose inhibits pigmentation caused by melanogenesis or inhibits tyrosinase activity, wherein the allulose is contained in an amount of 1-2 wt % with respect to 100 wt % of the composition.

2. A method for preventing or treating a pigmentation disease, the method comprising administering a composition comprising an effective amount of allulose to a subject in need thereof, wherein the allulose inhibits tyrosinase activity, wherein the allulose is contained in an amount of 1-2 wt % with respect to 100 wt % of the composition.

3. The method of claim 1, wherein the composition is a cosmetic, food, or pharmaceutical composition.

* * * * *